United States Patent [19]

Schilling

[11] 4,388,814
[45] Jun. 21, 1983

[54] CRYOGENIC DEVICE AND METHOD

[76] Inventor: Dean W. Schilling, 5049 Diane Dr., Minnetonka, Minn. 55343

[21] Appl. No.: 362,486

[22] Filed: Mar. 26, 1982

[51] Int. Cl.³ ............................................. F25D 25/00
[52] U.S. Cl. ......................................... 62/62; 62/78; 62/383; 62/514 R
[58] Field of Search .................. 62/62, 78, 383, 514 R

[56] References Cited

U.S. PATENT DOCUMENTS

| | | | |
|---|---|---|---|
| 3,195,620 | 7/1965 | Steinhardt, Jr. | 62/514 R |
| 3,916,640 | 11/1975 | Rasovich | 62/381 |
| 3,938,347 | 2/1976 | Riedel et al. | 62/49 |
| 4,306,425 | 12/1981 | Sitte et al. | 62/514 R |
| 4,314,450 | 2/1982 | Pelloux-Gervais | 62/514 R |

OTHER PUBLICATIONS

Schiling, D. W., *A Precision Temperature Control Mechanism for Vapour Freezing;* Abstract from Cryobiology, Dec. 1978.
Frim, J. et al., Controlled Variable-Rate Freeze Thaw Apparatus: Cryobiology 15, 317-322 (1978).

*Primary Examiner*—Ronald C. Capossela
*Attorney, Agent, or Firm*—James R. Haller

[57] ABSTRACT

The temperature of a biological specimen or other object may be controlled by supporting the object within a vessel containing a liquid cryogen above the liquid cryogen level and varying the vertical spacing between the object and the liquid cryogen level. The vessel is provided with vertically continuous inner walls of high thermal conductivity, e.g., metal walls, to provide a vertical temperature gradient within the vessel above the liquid cryogen level.

9 Claims, 3 Drawing Figures

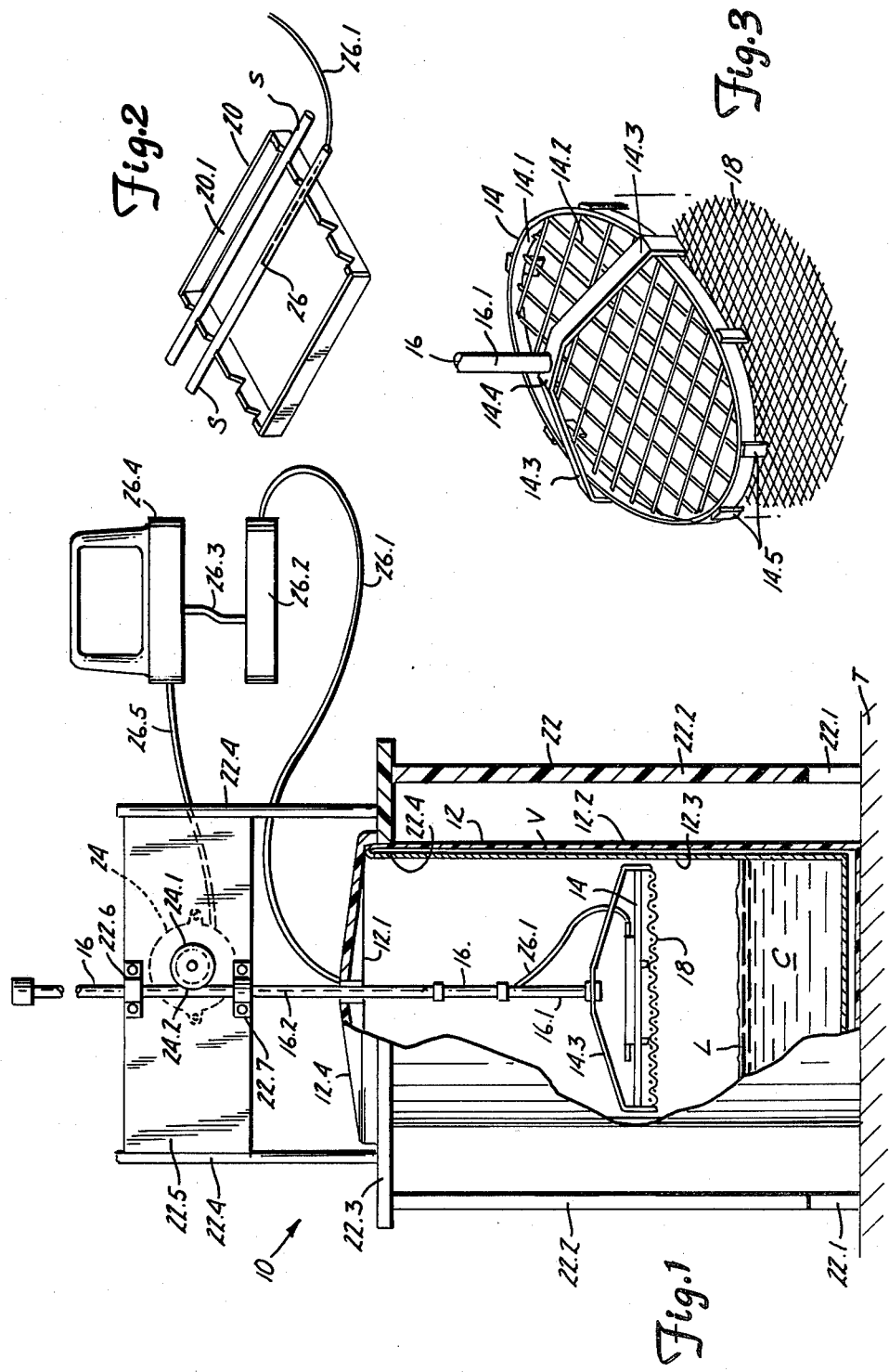

CRYOGENIC DEVICE AND METHOD

FIELD OF THE INVENTION

The invention relates to the field of cold temperature processing of materials, and particularly to the cryogenic treatment of biological specimens.

BACKGROUND OF THE INVENTION

Certain technological methods, particularly procedures involving biological materials, involve the use of cryogenic temperatures. For example, for stabilizing biological specimens for later microscopic examination, the specimens are often quickly frozen and the water in the samples is then exchanged or replaced with suitable organic solvents such as acetone at low temperatures. To reduce damage to the specimens, the substitution of an organic liquid for water often takes place at temperatures in the range of from about $-80°$ to about $-120°$ C., and this reduced temperature must be maintained over a period of time. As taught in U.S. Pat. No. 4,306,425 (Sitte, et al), the time required for such substitution may range from about three days to about three weeks. Various procedures in the field of genetic engineering require specimens to be subjected to cryogenic temperatures. For certain biological procedures, the time rate of cooling is of importance. Cryogenic temperatures may be used for storage of various biological materials such as heart valves, corneas, bone marrow cells, skin tissue, spermatozoa, etc.

Various devices have been proposed for enabling the temperature of a biological specimen or other material to be controllably lowered and maintained. Certain of such devices have employed, in combination, a cryogenic liquid or vapor to cool a specimen and a heater such as an electric resistance heater to heat the specimen, the specimen temperature being controlled, to the extent possible, by varying the amount of heat energy supplied to the specimen holder. Reference is made, for example, to the above-mentioned U.S. Pat. No. 4,306,425. It also has been proposed to suspend a specimen within a dewar flask above the level of liquid cryogen, and to raise and lower the specimen as desired to obtain the desired temperature or cooling rate.

The devices that utilize a cryogen for cooling a specimen in opposition to a heater for warming the specimen are commonly difficult to control. In one such device, for example, a cryogenic vapor is sprayed or evaporated into a compartment having electric heaters in its walls, the compartment having an interior fan for the purpose of equalizing the temperature throughout the compartment. This device is difficult to regulate with any degree of accuracy, since a large amount of time is required for the compartment to come to a steady state temperature, or to be varied from one temperature to another; that is, the response time of the apparatus is quite large. The positioning of a specimen at given levels within a dewar flask similarly is difficult to control, since the temperature gradient extending from the level of the liquid cryogen to the mouth of the flask generally is greatly compressed near the liquid level and accordingly the temperature varies greatly within a short space above the liquid level.

SUMMARY OF THE INVENTION

It has now been discovered that the linearity or uniformity of a vertical temperature gradient above the level of liquid cryogen in a dewar-type flask or other vessel can be vastly improved by utilizing a material of high thermal conductivity for the inner wall of the vessel. The thermal conductivity of the inner wall material desirably is not less than about 4.0 Btu-ft/(ft$^2$) (hr) (°F.); most preferably the inner wall is made of a metal such as stainless steel. The metal inner wall should be upwardly vertically continuous from a point adjacent or below the level of liquid cryogen in the vessel. Although it is desired that the inner wall be entirely of metal, such as stainless steel, the inner wall may have wall segments of metal or other material of high thermal conductivity extending upwardly from adjacent or below the liquid cryogen level. Although substantially any liquid cryogen can be employed, the most common liquid cryogens are liquid air and liquid nitrogen.

The invention hence provides a method for controlling the temperature of an object such as a biological specimen which comprises supporting the object in an upwardly open vessel containing a liquid cryogen, the vessel having vertically continuous inner walls of high thermal conductivity to provide a vertical temperature gradient above the level of the liquid cryogen, and varying the vertical spacing between the object and the cryogen liquid level (as by moving the object upwardly or downwardly within the vessel) to raise or lower, respectively, the temperature of the object. The method preferably includes the steps of sensing a temperature relative to the temperature of the object (that is, sensing the object temperature or the temperature of an adjacent structure such as a support carrying the specimen), the vertical spacing of the object above the liquid cryogen level being varied until the desired temperature is obtained.

The invention is readily adapted to automatic use in which the sensed temperature is compared with a desired temperature to generate a signal representative of the temperature difference, the means for varying the vertical spacing of the object being responsive to the signal so as to increase such spacing if the sensed temperature is lower than the desired temperature and to reduce such spacing if the sensed temperature is greater than the desired temperature. The desired temperature may be varied as desired; in a preferred embodiment in which the temperature of an object is to be varied as a function of time, the desired temperature may be varied in accordance with a pre-set program such as may be employed with a digital computer.

In another embodiment, the invention relates to a device for controlling the temperature of an object. The device comprises an upwardly open vessel containing a liquid cryogen, the vessel having vertically continuous inner walls of high thermal conductivity to produce a vertical temperature gradient within the vessel above the level of liquid cryogen. The device includes support means for supporting the object within the vessel above the level of liquid cryogen, and further includes elevation varying means for increasing and decreasing the vertical spacing between the support means and the cryogen liquid level to thus vary the temperature of the object. Preferably, the device includes temperature-sensing means carried by the support means for sensing a temperature related to the object temperature so that the object temperature may be closely followed. Desirably, control means are provided that are responsive to the temperature-sensing means for generating an electric signal characteristic of the difference between the sensed temperature and the desired temperature. The elevation varying means in this embodiment includes means responsive to the electric signal to vary the elevation of the support means within the vessel above the liquid cryogen level.

DESCRIPTION OF THE DRAWING

FIG. 1 is a partially broken-away front view in partial cross-section of a device of the invention;

FIG. 2 is a perspective view of a specimen or other object holder useful in the device of FIG. 1; and FIG. 3 is a perspective, exploded, partially broken-away view of a platform for use in the device of FIG. 1.

DETAILED DESCRIPTION

A device of the invention is shown generally as (10) in FIG. 1. A vessel (12) having an upwardly open top (12.1) is provided with an outer wall (12.2) of an insulating material such as plastic or cork or the like preferably having a coefficient of thermal conductivity less than about 0.5 Btu-ft/ (ft$^2$) (hr) (°F.). The inner wall (12.3) of the vessel is of a material of high thermal conductivity, preferably about 4.0 Btu-ft (ft$^2$) (hr) (°F.). The wall (12.3) preferably is of metal such as stainless steel. As shown in the drawing, the inner wall (12.3) is continuous about the interior of the vessel (12), and the vessel in effect comprises spaced, nested inner and outer vessels formed by the respective walls (12.3), (12.2), the space "v" between the walls being evacuated. It is important that the inner walls (12.3) be vertically continuous upwardly from a point adjacent or below the level L of liquid cryogen C as to a point adjacent the open end of the vessel; if desired, one may employ a vessel having interior walls including generally vertical strips or wall segments of a material such as metal having a high coefficient of thermal conductivity.

As will be explained more fully below, it is believed that the heat conductive inner walls (12.3) of the vessel conduct heat downwardly from the upper portions of the vessel and hence contribute importantly to a reasonably uniform temperature gradient above the cryogen liquid level L. If desired, the outer wall (12.2) may be spaced from the inner wall (12.3) to provide an air or vacuum space to thus reduce heat transfer inwardly through the walls of the vessel. The vessel (12) may take the form of a common dewar flask having an evacuated space between inner and outer walls and a glass interior, within which is fitted a metal container or vertical strips forming wall segments to thereby provide inner walls of high thermal conductivity. The level of liquid cryogen within the vessel (12) may be regulated by known means, such as that described in U.S. Pat. No. 3,938,347 (Riedel).

Support means, typified by a platform (14) in FIG. 1, is supported within the flask (12) above the liquid cryogen level L. The platform (14) preferably is circular with the edges of the platform closely spaced from the inner wall (12.3) of the vessel. As shown in FIG. 3, the platform (14) may be formed of a hoop (14.1) of plastic or similar material, and a supporting open gridwork, as shown at (14.2), may be cemented or otherwise affixed to the hoop to provide an open, porous floor upon which specimens or a specimen holder may be supported. In the embodiment of FIGS. 1 and 3, arms (14.3) extend upwardly and then inwardly from opposed sides of the hoop (14) and are joined by a support plate (14.4) which in turn is connected to the lower end (16.1) of a vertical support rod (16).

To reduce horizontal temperature gradients, that is, gradients extending generally transversely of the vessel (12), heat conduction means, typified by a wire grid (18), is carried by the platform (14) and is attached to the platform by connecting struts (14.5). The grid (18) desirably is spaced below the platform (14), as shown in FIG. 1, and the edges of the grid (18) desirably closely approach but do not touch the inner walls (12.3) of the vessel. Upon the supporting grid (14.2) may be placed a specimen holder such as that shown at (20) in FIG. 2. The specimen holder, as depicted, comprises a generally rectangular frame (20.1), opposite upper edges of which are notched or otherwise formed to receive glass specimen tubes S and to support the specimen tubes horizontally within the vessel.

The support rod (16) extends upwardly through the open upper end of the vessel (12), and is provided with a flat side (16.1) bearing teeth along its length, the latter being schematically depicted as (16.2) in FIG. 1. The open upper end (12.1) of the vessel may be partially closed by means of a lid or other cover typified by the split cover (12.4) in a manner known to the art, the support rod (16) passing upwardly without interference between the halves of the split cover (12.4).

A vertical stand (22) may be employed about the vessel (12), the stand having horizontally extending supports (22.1) at its bottom ends and upwardly extending frame members (22.2) terminating upwardly in a horizontal platform (22.3), the latter platform having a central opening (22.4) accommodating the vessel (12). The split cover (12.4) of the vessel typically may rest downwardly upon the rim at the open upper end of the flask, or may rest upon the platform (22.3). Extending upwardly from the platform (22.3) are support struts (22.4) between which is carried a support panel (22.5). To the support panel are attached bearing blocks (22.6, 22.7) through which slidably passes the support rod (16). Means for varying the vertical elevation of the platform is typified in FIG. 1 as including a stepping motor (24) mounted to and behind the support panel (22.5), the stepping motor having a shaft bearing a toothed gear (24.1), the teeth (24.2) of which mesh with the teeth (16.2) formed along the length of the support rod. In this manner, rotation of the gear (24.1) by the stepping motor in one direction or the other causes the support rod (16) and hence the platform (14) to be moved upwardly or downwardly within the vessel (12). Of course, other elevation varying means may also be employed. For example, the heighth of the liquid cryogen level may itself be varied by raising or lowering the vessel, or by varying the volume of liquid cryogen within the vessel.

Temperature-sensing means are depicted in FIGS. 1 and 2 as including a thermocouple (26) (shown in FIG. 2 as inserted within a tubular specimen holder S) having a lead (26.1) extending upwardly through the open top (12.1) of the vessel to a temperature-sensing device (26.2) which in turn is connected by a lead (26.3) to a controller (26.4), the temperature-sensing device (26.2) and controller (26.4) being common items of commerce. In a typical embodiment, the temperature-sensing device (26.2) produces a signal representative of the temperature at the level of the platform (14). The controller (26.4) electronically compares the sensed temperature with a preset or desired temperature and generates a signal representative of the difference between the sensed and desired or preset temperature, which signal is transmitted through lead (26.5) to the stepping motor (24), the latter being responsive to the signal to raise or lower the platform (14). As will now be understood, the platform will be raised upwardly to increase the sensed temperature, and downwardly to decrease the sensed temperature. Devices for producing a signal representative of a difference between desired and sensed temperatures are known in the art, and need not be described further. It will be understood that the support rod (16) may be manually moved upwardly or downwardly within the vessel (12) to increase or decrease the temperature of specimens carried by the platform. If desired, the controller (26.4) may be programmed in a known manner with a desired time rate of change of the desired temperature, as when a specimen is to be cooled or warmed at a predetermined rate. With respect to temperature sensors and controllers of this type, reference is made to U.S. Pat. No. 4,306,425, the teachings of which are incorporated herein by reference.

With reference to the embodiment shown in the drawing, a biological specimen may be inserted in one or more of the specimen tubes S, a neighboring tube bearing the end of a temperature-sensor such as a thermocouple. Good results have been obtained with a copper-constantan thermocouple made of 42 gauge wire and having an exceedingly small cold junction that is rapidly responsive to even small changes in cold junction temperature. If desired, the cold junction of the thermocouple may be attached to or embedded in the specimen. In either event, the cold junction is so placed that the temperature it senses is relative to; that is, approximately the same as or varying by a given amount from, the temperature of the specimen. The specimen holder (20) is then rested on the grid-work (14.2) of the platform (14) which in turn is carried adjacent the upper end of the vessel by the support rod (16). The lead (26.1) of the temperature sensor may be connected to, for example, a calibrated potentiometer from which the temperature of the specimen can be quickly determined. The platform is then lowered into the vessel (12), the bearings (22.6, 22.7) guiding the support rod (16) to maintain the edges of the platform spaced slightly inwardly of the inner wall (12.3) of the vessel. The support rod (16) may simply be positioned vertically by hand until the desired temperature is reached. For automatic control, the controller (26.4) (FIG. 1) provides an electric signal characteristic of the difference between the temperature that is sensed and a desired temperature, and the stepping motor (24) responds to the signal by raising or lowering the platform to bring the latter into warmer or colder regions of the vessel.

It is believed that the excellent and reasonably uniform vertical temperature gradient formed in the cryogen vapor space above the cryogen liquid level L is primarily due to the continuous transfer of heat downwardly through the highly conductive inner walls (12.3) of the vessel, and that a substantially steady state is reached when the transfer of heat downwardly through the walls (12.3), and inwardly from the side, bottom and top of the vessel is balanced by the heat of vaporization of the liquid cryogen and the resultant escape of cryogen vapor from the top of the vessel, neglecting radiation effects. There appears to be minimal convection within the cryogen vapor phase in the vessel. Heat from a specimen is believed to be lost primarily through conduction to the platform (14) and to the cryogen vapor, and by radiation to the vapor and to the inner walls (12.3) of the vessel. It will be understood that the vertical temperature gradient above the cryogen liquid level L need not be entirely uniform or linear, but uniformity and linearity is greatly increased through the use of the inner, highly conductive walls (12.3) of the vessel.

Although the invention has been described primarily with reference to the embodiments shown in FIGS. 1-3, inclusive, it will be understood that a wide variety of platforms, platform geometries and means for raising and lowering the platforms may be employed. The vessel (12) need not be cylindrical, as depicted in the drawing, may have other configurations; for example, the walls may taper inwardly near the top of the vessel in a manner common to cryogenic vessels.

While a preferred embodiment of the present invention has been described, it should be understood that various changes, adaptions and modifications may be made therein without departing from the spirit of the invention and the scope of the appended claims.

What is claimed is:

1. Method of controlling the temperature of an object comprising
  (a) providing an upwardly open vessel containing a liquid cryogen, the vessel having vertically continuous inner walls of high thermal conductivity to provide a vertical temperature gradient above the level of liquid cryogen,
  (b) supporting the object within the container above the liquid cryogen, and sensing a temperature relative to the temperature of the object, and
  (c) varying the vertical spacing of the object above the liquid cryogen level until the desired temperature is obtained.

2. Method of controlling the temperature of an object, comprising
  (a) providing an upwardly open vessel containing a liquid cryogen and having vertically continuous inner walls of high thermal conductivity to provide a vertical temperature gradient above the level of liquid cryogen in the vessel,
  (b) supporting the object within the vessel above the liquid cryogen level, and sensing a temperature relative to the temperature of the object,
  (c) comparing the sensed temperature with a desired temperature and generating a signal representing the difference in temperatures; and
  (d) providing means responsive to said signal for varying the vertical spacing of the object above the liquid cryogen so as to increase such spacing if the sensed temperature is lower than the desired temperature, and to decrease such spacing if the sensed temperature is greater than the desired temperature.

3. Method of controlling the temperature of an object which comprises supporting the object in an upwardly open vessel containing a liquid cryogen, the level of which is vertically spaced below the object, the vessel having vertically continuous inner walls of high thermal conductivity to provide a vertical temperature gradient above the level of liquid cryogen in the vessel, and varying the vertical spacing between the object and the cryogen liquid level within the vessel to raise or lower the temperature of the object.

4. Device for controlling the temperature of an object comprising
  (a) an upwardly open vessel containing a liquid cryogen, the vessel having vertically continuous inner walls of high thermal conductivity to provide a vertical temperature gradient within the vessel above the level of liquid cryogen;

(b) support means for supporting the object within the vessel above the level of liquid cryogen, and (c) elevation varying means for varying the vertical spacing of the support means above the liquid cryogen level to vary the temperature of the object.

5. The device of claim 4 including temperature-sensing means carried by the support means for sensing a temperature related to the object temperature.

6. The device of claim 5 including control means responsive to said temperature-sensing means for generating an electric signal characteristic of the difference between the sensed temperature and a desired temperature, said elevation varying means including means responsive to said electric signal to vary the elevation of said support means within the vessel above the liquid cryogen level.

7. The device of claim 4 in which the inner walls of the vessel are characterized by a thermal conductivity of not less than about 4.0 Btu-ft/(ft$^2$) (hr) (°F.).

8. The device of claim 6 including means for varying the desired temperature as a function of time.

9. The device of claim 4 including heat conduction means carried generally horizontally within the vessel by the support means for conducting heat inwardly of the vessel to reduce horizontal temperature gradients.

* * * * *